US006043260A

United States Patent [19]
Chen et al.

[11] Patent Number: 6,043,260
[45] Date of Patent: Mar. 28, 2000

[54] METHOD OF TREATING HEART FAILURE

[75] Inventors: Yuhpyng L. Chen, Waterford; Anthony A. Fossa, Stonington, both of Conn.

[73] Assignee: Pfizer Inc, New York, N.Y.

[21] Appl. No.: 09/248,073

[22] Filed: Feb. 10, 1999

Related U.S. Application Data

[60] Provisional application No. 60/074,934, Feb. 17, 1998.
[51] Int. Cl.[7] .................................................. A61K 31/44
[52] U.S. Cl. ............................................................ 514/348
[58] Field of Search .............................................. 514/348

[56] References Cited

FOREIGN PATENT DOCUMENTS

| 0773023 | 5/1997 | European Pat. Off. ..... A61K 31/435 |
| 9533750 | 12/1995 | WIPO .......................... C07D 487/04 |

OTHER PUBLICATIONS

Laurel A. Fisher, CRF and Autonomic and Cardiovascular Functioning, pp. 243–257, 1993.
Elvira Rohde, et al., Biochemical Pharmacology, Vo. 52., pp. 829–833, 1996.

*Primary Examiner*—Raymond Henley, III
*Attorney, Agent, or Firm*—Peter C. Richardson; Gregg C. Benson; Martha A. Gammill

[57] ABSTRACT

This invention relates to method for treating a mammal which presents with heart failure comprising administering to a mammal a therapeutically effective amount of wherein 4-(1-ethyl-propoxy)-3,6-dimethyl-2-(2,4,6-trimethyl-phenoxy)-pyridine and (3,6-dimethyl-2-(2,4,6-trimethyl-phenoxy)-pyridin-4-yl)-(1-ethyl-propyl)-amine or a pharmaceutically acceptable salt thereof. This invention is also directed to methods of using combinations of those two agents with other congestive heart failure treating compounds to treat congestive heart failure.

43 Claims, No Drawings

METHOD OF TREATING HEART FAILURE

This Application claims benefit of Provisional Application Ser. No. 60/074,934 Feb. 17, 1998

BACKGROUND OF INVENTION

This invention relates to the corticotropin releasing hormone (CRH) compounds 4-(1-ethyl-propoxy)-3,6-dimethyl-2-(2,4,6-trimethyl-phenoxy)-pyridine and (3,6-dimethyl-2-(2,4,6-trimethyl-phenoxy)-pyridin-4-yl)-(1-ethyl-propyl)-amine and the use thereof in treating heart failure.

The impact of heart failure continues to increase. Approximately three percent of the adult U.S. population (three to four million patients) have heart failure. With a steadily aging population, four hundred thousand individuals experience new onset heart failure each year, with a five year mortality rate approaching fifty percent. In 1991, alone, 2,280,445 patients were discharged from non-federal U.S. hospitals with a diagnosis of heart failure.

Congestive heart failure, regardless of its etiology, is characterized by a weakness of the myocardial tissue of the left and/or right ventricles of the heart to pump and circulate blood into systemic and/or pulmonary circulations. It is accompanied by circulatory and neurohumoral changes which result in failure to deliver sufficient blood and oxygen supply to peripheral tissues and vital organs. If left untreated the health of a patient with congestive heart failure could deteriorate to the point where the disease would be fatal. Congestive heart failure may be expressed as shortness of breath either on exertion, at rest or paroxysmal nocturnal dyspnea.

While angiotensin converting enzyme (ACE) inhibitors have been shown to demonstrate a significant reduction in both hospitalization and mortality in congestive heart failure patients, diuretics and digoxin continue to be more highly prescribed agents most likely due to their ability to provide effective symptomatic relief. However, digoxin's use is limited because of its slow onset of action and the small difference between the maximum therapeutic and minimum toxic dose levels. Moreover, the improved survival in patients treated with ACE inhibitors occurs primarily in the initial twelve months of therapy. Thus, a truly dramatic impact on disease progression has yet to be realized.

4-(1-Ethyl-propoxy)-3,6-dimethyl-2-(2,4,6-trimethyl-phenoxy)-pyridine and (3,6-dimethyl-2-(2,4,6-trimethyl-phenoxy)-pyridin-4-yl)-(1-ethyl-propyl)-amine are disclosed in International Patent Application Publication No. WO95/33,750 as having activity as a corticotropin releasing factor antagonist and, accordingly, utility in the treatment of a wide range of stress-related illnesses such as depression, anxiety, headache, irritable bowel syndrome, inflammatory diseases, immune suppression, Alzheimer's disease, gastrointestinal diseases, anorexia nervosa, hemorrhagic stress, drug and alcohol withdrawal symptoms, drug addiction, infertility, head trauma, stroke, and stress-induced infections in humans and animals.

4-(1-Ethyl-propoxy)-3,6-dimethyl-2-(2,4,6-trimethyl-phenoxy)-pyridine and (3,6-dimethyl-2-(2,4,6-trimethyl-phenoxy)-pyridin-4-yl)-(1-ethyl-propyl)-amine are also disclosed as part of a genus of compounds in International Patent Application Publication No. EP 07773023 as having utility in the treatment of a wide variety of cardiovascular or heart related diseases such as hypertension, tachycardia, congestive heart failure, stroke, osteoporosis, premature birth, psychosocial dwarfism, stress-induced fever, ulcer, diarrhea, post-operative ileus, and colonic hypersensitivity associated with psychopathological disturbance and stress.

Thus, although there are a variety of treatments for congestive heart failure there is a continuing need and a continuing search in this field of art for alternative therapies.

SUMMARY OF THE INVENTION

This invention is directed to methods for treating heart failure in animals, and particularly mammals, comprising administering to said animal a therapeutically effective amount of 4-(1-ethyl-propoxy)-3,6-dimethyl-2-(2,4,6-trimethyl-phenoxy)-pyridine, (3,6-dimethyl-2-(2,4,6-trimethyl-phenoxy)-pyridin-4-yl)-(1-ethyl-propyl)-amine, a prodrug thereof, or a pharmaceutically acceptable salt thereof or of said prodrug.

In a preferred aspect of this invention, designated Method A, 4-(1-ethyl-propoxy)-3,6-dimethyl-2-(2,4,6-trimethyl-phenoxy)-pyridine or a pharmaceutically acceptable salt thereof is administered.

4-(1-Ethyl-propoxy)-3,6-dimethyl-2-(2,4,6-trimethyl-phenoxy)-pyridine has the structure of Formula I below:

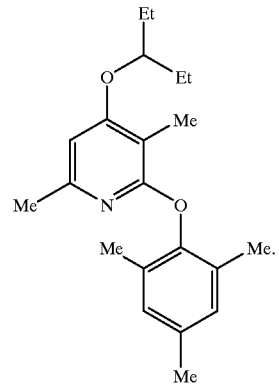

In a preferred aspect of Method A, 4-(1-ethyl-propoxy)-3,6-dimethyl-2-(2,4,6-trimethyl-phenoxy)-pyridine is adminstered.

In another preferred aspect of Method A, the mammal is a human.

In yet another preferred aspect of Method A, the mammal is a companion animal. The phrase "companion animal" refers to a household pet or other domesticated animal such as, but not limited to, cattle, sheep, ferrets, swine, horses, poultry, fish, rabbits, goats, dogs, cats and the like. Particularly preferred companion animals are dogs and cats.

In yet another preferred aspect of Method A, designated Method B, the heart failure is congestive heart failure.

In a preferred aspect of Method B, 4-(1-ethyl-propoxy)-3,6-dimethyl-2-(2,4,6-trimethyl-phenoxy)-pyridine is adminstered.

In another preferred aspect of Method B, designated Method C, the mammal is a human.

In another preferred aspect of Method B, the mammal is a companion animal.

In a preferred aspect of Method C, the congestive heart failure does not worsen.

In another preferred aspect of the method of this invention, designated Method D, (3,6-dimethyl-2-(2,4,6-trimethyl-phenoxy)-pyridin-4-yl)-(1-ethyl-propyl)-amine or a pharmaceutically acceptable salt thereof is administered.

(3,6-Dimethyl-2-(2,4,6-trimethyl-phenoxy)-pyridin-4-yl)-(1-ethyl-propyl)-amine has the structure of Formula II below:

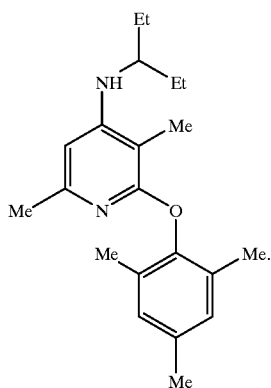

In a preferred aspect of Method D, (3,6-dimethyl-2-(2,4,6-trimethyl-phenoxy)-pyridin-4-yl)-(1-ethyl-propyl)-amine is administered.

In another preferred aspect of Method D, the mammal is a human.

In yet another preferred aspect of Method D, the mammal is a companion animal.

In yet another preferred aspect of Method D, designated Method E, the heart failure is congestive heart failure.

In a preferred aspect of Method E, designated Method E, (3,6-dimethyl-2-(2,4,6-trimethyl-phenoxy)-pyridin-4-yl)-(1-ethyl-propyl)-amine is administered.

In a preferred aspect of Method F, designated Method G, the mammal is a human.

In another preferred aspect of Method F, the mammal is a companion animal.

In a preferred aspect of Method G, the congestive heart failure does not worsen.

A pharmaceutical composition comprising (a) 4-(1-ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propoxy)-amine, a prodrug thereof or a pharmaceutically acceptable salt thereof or of said prodrug, (b) a congestive heart failure treating agent and (c) a pharmaceutically acceptable carrier or diluent.

This invention is also directed to those pharmaceutical compositions set forth in the immediately preceding paragraph wherein said congestive heart failure treating agent is a cardiac glycoside, a loop diuretic, a thiazide diuretic, a potassium ion sparing diuretic, an angiotensin converting enzyme inhibitor, an angiotension receptor antagonist, a nitrovasodilator, a phosphodiesterase inhibitor, a direct vasodilator, an $\alpha_1$-adrenergic receptor antagonist, a calcium channel blocker or a sympathomimetic agent.

A preferred pharmaceutical composition of this invention, designated Composition A, comprises 4-(1-ethyl-propoxy)-3,6-dimethyl-2-(2,4,6-trimethyl-phenoxy)-pyridine.

A more preferred aspect of Composition A, designated Composition B, comprises the mesylate salt of 4-(1-ethyl-propoxy)-3,6-dimethyl-2-(2,4,6-trimethyl-phenoxy)-pyridine.

A preferred aspect of Composition B is wherein said calcium channel blocker is amlodipine.

Another preferred pharmaceutical composition of this invention, designated Composition C, comprises (3,6-dimethyl-2-(2,4,6-trimethyl-phenoxy)-pyridin-4-yl)-(1-ethyl-propoxy)-amine or a pharmaceutically acceptable salt thereof.

A preferred aspect of Composition C, designated Composition D, comprises wherein (3,6-dimethyl-2-(2,4,6-trimethyl-phenoxy)-pyridin-4-yl)-(1-ethyl-propoxy)-amine is administered.

A preferred aspect of Composition D is wherein said calcium channel blocker is amlodipine.

This invention is further directed to a method, designated Method H, for treating heart failure in a mammal comprising administering to said mammal a pharmaceutical composition comprising (a) 4-(1-ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propoxy)-amine, a prodrug thereof or a pharmaceutically acceptable salt thereof or of said prodrug, (b) a congestive heart failure treating agent and (c) a pharmaceutically acceptable carrier or diluent.

A preferred aspect of Method H, designated Method I, is wherein said congestive heart failure treating agent is a cardiac glycoside, a loop diuretic, a thiazide diuretic, a potassium ion sparing diuretic, an angiotensin converting enzyme inhibitor, an angiotension receptor antagonist, a nitrovasodilator, a phosphodiesterase inhibitor, a direct vasodilator, an $\alpha_1$-adrenergic receptor antagonist, a calcium channel blocker or a sympathomimetic agent.

A preferred aspect of Method I, designated Method J, method of claim 27 comprises 4-(1-ethyl-propoxy)-3,6-dimethyl-2-(2,4,6-trimethyl-phenoxy)-pyridine or a pharmaceutically acceptable salt thereof.

A preferred aspect of Method J, designated Method K, is wherein the mesylate salt of 4-(1-ethyl-propoxy)-3,6-dimethyl-2-(2,4,6-trimethyl-phenoxy)-pyridine is administered.

A preferred aspect of Method K is wherein said calcium channel blocker is amlodipine.

Another preferred aspect of Method H, designated Method L, comprises (3,6-dimethyl-2-(2,4,6-trimethyl-phenoxy)-pyridin-4-yl)-(1-ethyl-propoxy)-amine or a pharmaceutically acceptable salt thereof.

A preferred aspect of Method L, designated Method M, is wherein (3,6-dimethyl-2-(2,4,6-trimethyl-phenoxy)-pyridin-4-yl)-(1-ethyl-propoxy)-amine is administered.

A preferred aspect of Method M is wherein said calcium channel blocker is amlodipine.

This invention is also directed to a kit comprising
a. an amount of a compound, said compound being selected from 4-(1-ethyl-propoxy)-3,6-dimethyl-2-(2,4,6-trimethyl-phenoxy)-pyridine, (3,6-dimethyl-2-(2,4,6-trimethyl-phenoxy)-pyridin-4-yl)-(1-ethyl-propoxy)-amine, a prodrug thereof, and a pharmaceutically acceptable salt of said compound or said salt in a first unit dosage form;
b. an amount of a congestive heart failure treating agent; and
c. a container.

It is preferred that said congestive heart failure treating agent portion of said kit is a cardiac glycoside, a loop diuretic, a thiazide diuretic, a potassium ion sparing diuretic, an angiotensin converting enzyme inhibitor, an angiotension receptor antagonist, a nitrovasodilator, a phosphodiesterase inhibitor, a direct vasodilator, an $\alpha_1$-adrenergic receptor antagonist, a calcium channel blocker or a sympathomimetic agent.

It is especially preferred that said kit comprises 4-(1-ethyl-propoxy)-3,6-dimethyl-2-(2,4,6-trimethyl-phenoxy)-pyridine or a pharmaceutically acceptable salt thereof.

It is still more especially preferred that said kit comprises 4-(1-ethyl-propoxy)-3,6-dimethyl-2-(2,4,6-trimethyl-phenoxy)-pyridine.

It is still more especially preferred that in said kit, said calcium channel blocker is amlodipine.

It is also especially preferred that the kit comprises (3,6-dimethyl-2-(2,4,6-trimethyl-phenoxy)-pyridin-4-yl)-(1-ethyl-propoxy)-amine.

It is especially preferred that said kit comprises (3,6-dimethyl-2-(2,4,6-trimethyl-phenoxy)-pyridin-4-yl)-(1-ethyl-propoxy)-amine.

It is still more especially preferred that in said kit, said calcium channel blocker is amlodipine.

Heart failure refers to conditions in which the heart is no longer able to pump an adequate supply of blood in relation to the venous return and in relation to the metabolic needs of the tissues of the body at that particular moment.

Congestive heart failure refers to that state in which abnormal circulatory congestion occurs as the result of heart failure. This includes but is not limited to circulatory failure due to mechanical abnormalities, myocardial (muscular) failure, peripheral circulatory failure and cardiac and non-cardiac circulatory overload.

The term "treating", "treat" or "treatment" as used herein includes curative, preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or a mixture of solvents which does not interact with starting materials, reagents, intermediates or products in a manner which adversely affects the yield of the desired product.

Other features and advantages will be apparent from the specification and claims which describe the invention.

DETAILED DESCRIPTION OF THE INVENTION

As mentioned above, 4-(1-ethyl-propoxy)-3,6-dimethyl-2-(2,4,6-trimethyl-phenoxy)-pyridine is known in the art. 4-(1-Ethyl-propoxy)-3,6-dimethyl-2-(2,4,6-trimethyl-phenoxy)-pyridine is claimed and its preparation is described in International Patent Application Publication No. WO95/33,750. The preparation of 4-(1-ethyl-propoxy)-3,6-dimethyl-2-(2,4,6-trimethyl-phenoxy)-pyridine is set forth in the Example section below.

Generally, 3-pentanol is dissolved in a reaction inert solvent such as dimethylsulfoxide or 1-methyl-2-pyrrolidinone and is reacted with a suitable base such as potassium t-butoxide, potassium hydride or sodium hydride. The reaction mixture is stirred at about 0° C. to about room temperature, preferably at room temperature, for about zero minutes to about one hour, preferably for about fifteen minutes to about thirty minutes. A solution of 4-chloro-2,5-dimethyl-6-(2,4,6-trimethylphenoxy)-pyridine or 4-bromo-2,5-dimethyl-6-(2,4,6-trimethylphenoxy)-pyridine in a reaction inert solvent such as tetrahydrofuran, dimethylsulfoxide or 1-methyl-2-pyrrolidinone or a mixture of THF with DMSO or with 1-methyl-2-pyrrolidinone is added. Alternatively, a mixture of 3-pentanol and 4-chloro-2,5-dimethyl-6-(2,4,6-trimethylphenoxy)-pyridine or 4-bromo-2,5-dimethyl-6-(2,4,6-trimethylphenoxy)-pyridine in a reaction inert solvent may be treated portionwise with a suitable base such as potassium t-butoxide, potassium hydride or sodium hydride at 0° C. to room temperature until all hydrogen generated by the reaction has evolved. Preferably the reaction is carried out at room temperature. The resulting mixture is heated at about 80° C. to about 130° C., preferably at 130° C. for about one hour to about sixteen hours, preferably for about three hours. The product is isolated according to procedures well known to those skilled in the art.

As mentioned above (3,6-dimethyl-2-(2,4,6-trimethyl-phenoxy)-pyridin-4-yl)-(1-ethyl-propyl)-amine is also known in the art. (3,6-Dimethyl-2-(2,4,6-trimethyl-phenoxy)-pyridin-4-yl)-(1-ethyl-propyl)-amine is claimed and its preparation is described in International Patent Application Publication No. WO95/33,750. The following description is provided for the preparation of (3,6-dimethyl-2-(2,4,6-trimethyl-phenoxy)-pyridin-4-yl)-(1-ethyl-propyl)-amine.

(3,6-dimethyl-2-(2,4,6-trimethyl-phenoxy)-pyridin-4-yl)-(1-ethyl-propyl)-amine is prepared by reacting 4-(1-ethyl-propylamino)-6-methyl-2-(2,4,6-trimethyl-phenoxy)-nicotinic acid methyl ester with a suitable reducing agent in a reaction inert solvent. A particularly preferred reducing agent is lithium aluminum hydride in the presence of aluminum trichloride. A particularly preferred solvent is dry tetrahydrofuran. The product is isolated from the reaction mixture according to well-known techniques of organic chemistry.

Alternatively, (3,6-dimethyl)-2-(2,4,6-trimethyl-phenoxy)-pyridin-4-yl)-1-ethyl-propyl)-amine is prepared by reacting 4-bromo-2,5-dimethyl-6-(2,4,6-trimethylphenoxy-pyridine with 1-ethylpropylamine in the presence of two mole percent to one equivalent of a one to one ratio of (S)- or (R)-BINAP (also known as 2,2'-bis(diphenylphosphino)-1,1'-binaphthyl) and Pd(OAc)$_2$ and one to two equivalents (preferably one equivalent) of potassium t-butoxide in a reaction inert solvent such as toluene at a temperature of between 80° C. to about 140° C., preferably at the reflux temperature of the reaction mixture.

4-(1-Ethyl-propylamino)-6-methyl-2-(2,4,6-trimethyl-phenoxy)-nicotinic acid methyl ester is prepared according to procedures well known to those skilled in the art. An exemplary procedure is set forth in the Preparation section below.

The starting materials, intermediates and reagents used to prepare the above described compounds are readily available or can be easily synthesized by those skilled in the art using conventional methods of organic synthesis. The preparation of certain reagents and intermediates is set forth in the Preparations section below.

The pharmaceutically acceptable acid addition salts of compounds of formulas I and II of this invention are also within the scope of this invention. Such pharmaceutically acceptable acid addition salts can be prepared in a conventional manner by treating a solution or suspension of the corresponding formula I or formula II free base with one chemical equivalent of a pharmaceutically acceptable acid. Conventional concentration or crystallization techniques can be employed to isolate such salts. Illustrative of suitable pharmaceutically acceptable acids are acetic, lactic, succinic, maleic, tartaric, citric, gluconic, ascorbic, benzoic, cinnamic, fumaric, sulfuric, phosphoric, hydrochloric, hydrobromic, hydriodic, sulfamic, sulfonic acids and related acids as well as methanesulfonic, benzenesulfonic, p-toluenesulfonic acids and related acids.

The second compound of this invention may be basic or acidic and as such it may form salts with either pharmaceutically acceptable anions or cations. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The utility of the compounds of the present invention as a medical agent in the treatment of heart failure in mammals (e.g. humans) is demonstrated by the activity of the compounds of this invention in conventional assays described below. Such assays also provide a means whereby the activities of the compounds of this invention can be compared with the activities of other known compounds. The results of these comparisons are useful for determining dosage levels in mammals, including humans, for the treatment of such diseases.

Receptor Binding. P2 membranes (1 mg wet weight/mL) from human neuroblastoma IMR32 cells are prepared in buffer (20 mM 1,4-piperazinediethanesulfonic acid (Pipes, pH 7.0), 10 nM $MgCl_2$, 2 mM EGTA, 0.04% BSA, 0.015% bacitracin, 100 units/mL aprotinin). Aliquots of 100 μl are added to assay samples containing $^{125}$I-labeled ovine CRF ($^{125}$I-oCRF; 40 pM) and test compounds or buffer in a final volume of 200 μl. Nonspecific binding is determined using 1 μM rat/human CRF. After a 2 hour incubation at room temperature, assay samples are centrifuged for 10 minutes at 1300×g. The supernatant is discarded. Samples are rinsed with 100 μl of ice-cold assay buffer and recentrifuged. Pellets are filtered onto Betaplate filtermats using a Skatron cell harvester (setting 222). Radioactivity is quantified using a Betaplate scintillation counter (LKB).

Other methods that may be used to determine the CRF antagonist activity of the compounds and combinations of this invention and their pharmaceutically acceptable salts are described in *Endocrinology*, 116, 1653–1659 (1985) and *Peptides*, 10, 179–188 (1985). The binding activities for the compounds of this invention and their pharmaceutically acceptable salts, expressed as $IC_{50}$ values, generally range from about 0.5 nanomolar to about 10 micromolar.

The compounds of this invention are readily adapted to clinical use as a heart failure treating agent.

To treat heart failure, an amount of 4-(1-ethyl-propoxy)-3,6-dimethyl-2-(2,4,6-trimethyl-phenoxy)-pyridine, (3,6-dimethyl-2-(2,4,6-trimethyl-phenoxy)-pyridin-4-yl)-(1-ethyl-propyl)-amine, a prodrug thereof or a pharmaceutically acceptable salt thereof or of said prodrug that is effective for the heart failure treatment of this invention, for example congestive heart failure treatment is used. Typically, an effective dosage of 4-(1-ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propyl)-amine for a 50 kg to 100 kg human being is in the range of about 0.1 mg to 3000 mg per day in single or divided doses, and preferably about one mg to about 1000 mg per day in single or divided doses. An especially preferred dosage range is 10 mg to 100 mg per day in single or divided doses. It will be recognized by a person skilled in the art that, in accordance with this invention, a pharmaceutically acceptable salt of the compounds of the invention may be administered. Dosages of said salts can be readily calculated by persons skilled in the art by application of simple mathematical and chemical principles.

The amount and timing of compound administered will be dependent upon the subject being treated, on the severity of the affliction, on the manner of administration and upon the judgment of the prescribing physician. Thus, due to patient to patient variability, the dosages given above are intended to be a guideline. The physician may titrate doses of 4-(1-ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propyl)-amine to achieve the treatment (e.g., congestive heart failure improvement) that the physician considers appropriate for the patient. In considering the degree of treatment desired, the physician must balance a variety of factors such as age of the patient, presence of preexisting disease, as well as presence of other diseases.

4-(1-Ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propyl)-amine may be administered alone or in combination with digitalis, thiazide diuretics, other diuretics and ACE inhibitors.

The compounds of the present invention are generally administered in the form of a pharmaceutical composition comprising 4-(1-ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propyl)-amine together with a pharmaceutically acceptable carrier or diluent. Thus, 4-(1-ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propyl)-amine can be administered individually or together in any conventional oral, parenteral, rectal or transdermal dosage form.

The compounds of the present invention and their pharmaceutically acceptable salts may be administered alone or in combination with pharmaceutically acceptable carriers, in either single or multiple doses. Suitable pharmaceutical carriers include inert solid diluents or fillers, sterile aqueous solutions, oils (e.g., peanut oil, sesame oil) and various organic solvents. The pharmaceutical compositions formed by combining a compound of the present invention and pharmaceutically acceptable carriers can then be readily administered in a variety of dosage forms such as tablets, powders, lozenges, emulsions, oil soft gels, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules.

Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 18th Edition (1990).

Pharmaceutical compositions according to this invention may contain 0.1%–95% of a compound of this invention, preferably 1%–70%. In any event, the composition or formulation to be administered will contain a quantity of a compound according to this invention in an amount effective to treat the disease/condition of the subject being treated, e.g., congestive heart failure.

Since the present invention relates to the treatment of diseases and conditions with a combination of active ingredients which may be administered separately, the invention also relates to combining separate pharmaceutical compositions in kit form. The kit includes two separate pharmaceutical compositions: 4-(1-ethyl-propoxy)-3,6-dimethyl-2-(2,4,6-trimethyl-phenoxy)-pyridine, (3,6-dimethyl-2-(2,4,6-trimethyl-phenoxy)-pyridin-4-yl)-(1-ethyl-propoxy)-amine, a prodrug thereof, or a pharmaceutically acceptable salt of said compound and a congestive heart failure treating agent. The kit includes container means for containing the separate compositions such as a divided bottle or a divided foil packet, however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Where used herein, the terms "THF" and "DMSO" mean "tetrahydrofuran" and "dimethylsulfoxide", respectively.

The present invention is illustrated by the following Examples. However, it should be understood that the invention is not limited to the specific details of these Examples.

EXAMPLE 1

4-(1-Ethyl-propoxy)-3,6-dimethyl-2-(2,4,6-trimethyl-phenoxy)-pyridine. To a solution of 3-pentanol (56 mL, 0.5205 mol) in dimethyl sulfoxide (DMSO, 760 mL) was added, portionwise, sodium hydride (60% oil dispersion, 7.64 g, 0.191 mol). After stirring at room temperature for thirty minutes, a solution of 4-chloro-2,5-dimethyl-6-(2,4,6-trimethylphenoxy)-pyridine (prepared as described in Preparation D, 47.80 g, 0.1735 mol) in tetrahydrofuran (THF, 50 mL) was added and the resulting mixture was heated at 130° C. for three hours. The mixture was quenched with water and extracted with ethyl acetate. The organic layer was separated, dried and concentrated to give 68.21 g of a yellow solid. The solid was purified through silica gel column chromatography using 10% chloroform in hexane to chloroform as eluent to give 52.2064 g (92%) of the title compound of Example 2 as white crystals. mp 72.5° C. to 74° C. $^1$HNMR (CDCl$_3$) δ 6.84 (s, 2H), 6.26 (s,1 H), 4.16 (m, 1H), 2.27 (s, 3H), 2.17 (s, 6H), 2.04 (s, 6H), 1.69 (m, 4H), 0.95 (t, 6H) ppm.

EXAMPLE 2

4-(1-Ethyl-propoxy)-3,6-dimethyl-2-(2,4,6-trimethyl-phenoxy)-pyridinium methanesulfonate. 4-(1-ethyl-propoxy)-3,6-dimethyl-2-(2,4,6-trimethyl-phenoxy)-pyridine (prepared as described in Example 1) was treated with 1 equivalent of methanesulfonic acid in ethyl acetate. The white crystals formed from ethyl acetate, melting point 117–119° C.

EXAMPLE 3

[3,6-Dimethyl-2-(2,4,6-trimethyl-phenoxy)-pyridin-4-yl]-(1-ethyl-propyl)-amine. To a mixture of 4-(1-ethyl-propylamino)-6-methyl-2-(2,4,6-trimethyl-phenoxy)-nicotinic acid methyl ester (prepared as described in Preparation F, 29 mg, 0.078 mmol) and AlCl$_3$ (10 mg, 0.078 mmol) in dry THF was added 1 M LiAlH$_4$ in diethyl ether (0.31 ml, 0.31 mmol) at room temperature. After stirring for 10 min, the mixture was heated under reflux for 2 hr. The mixture was quenched with 0.2 ml of water, 0.2 ml of 1N NaOH and 0.4 ml of water and 10 ml of dry THF and stirred for 15 min. The mixture was filtered through Celite® and washed with chloroform. The filtrate was dried over dry sodium sulfate, filtered and concentrated to dryness to give 26 mg (93%) of white solid. $^1$H NMR (CD$_{C13}$) δ 6.85(s,2H), 6.08(s,1H), 3.72(d,NH, 1H), 3.35(m,1H), 2.30(s,3H), 2.16 (s,3H), 2.13 (s,3H), 2.05(s, 6H), 1.45–1.75(m,4H), 0.98(t, 6H) ppm. The corresponding HCl salt was prepared and triturated with diethyl ether to give white solid, mp.212–215° C.

Preparation A 2,4-Dichloro-3,6-dimethylpyridine. A mixture of 2,4-dihydroxy-3,6-dimethylpyridine (2.86 g, 20.58 mmol), POCl$_3$ (15 ml) and N,N-diethylaniline (3.6 ml, 22.64 mmol) was heated under reflux for 3 hours. The mixture was cooled, poured into ice water and extracted with diethyl ether. The organic layer was dried and concentrated to give 3.02 g of the crude material. After silica gel column chromatography using chloroform as eluent, 1.3102 g of the title compound was obtained as a yellow oil. $^1$HNMR (CDCl$_3$) δ 7.07 (s, 1H), 2.43 (s, 3H), 2.39 (s, 3H) ppm.

Preparation B

4-Chloro-3,6-dimethyl-2-(2,4,6-trimethyl-phenoxy)-pyridine. Pyridine (250 mL) was added to a 2 liter flask equipped with a mechanical stirrer, a reflux condenser and a nitrogen inlet. The flask was cooled in an ice bath and 2,4,6-trimethylphenol (42.5 g, 0.312 mol) and potassium t-butoxide (35.1 g, 0.313 mol) were added. The flask was warmed to room temperature and 2,4-dichloro-3,6- dimethylpyridine (50.0 g, 0.284 mol) and copper (I) iodide (13.5 g, 0.071 mol) were added. The reaction mixture was heated under reflux for two hours and then cooled to 0° C. The reaction mixture was diluted with hexanes (500 mL) and mixed with saturated ammonium chloride ($NH_4Cl$, 1000 mL). After warming to room temperature, the mixture was stirred overnight. The layers were separated and the organic layer was washed with 3×125 mL of 1N hydrochloric acid (HCl) and 1×250 mL of water. After drying over sodium sulfate ($Na_2SO_4$), the solids were removed by filtration and washed with hexanes. The filtrate was concentrated under vacuum to afford a brown oil. The residue was mixed with methanol (250 mL) and was stirred overnight. The resulting slurry was filtered under vacuum. The off-white solids were washed with methanol then dried to afford 31.6 g (40.4%) of the title compound of Preparation F. $^1$HNMR ($CDCl_3$): δ 6.88 (s, 2H), 6.78 (s, 1H), 2.40 (s, 3H), 2.30 (s, 3H), 2.20 (s, 3H), 2.04 (s, 6H).

The filtrate was concentrated under vacuum to afford an oil and the residue was mixed with methanol (50 mL). After stirring overnight, the resulting slurry was cooled to 0° C. and filtered under vacuum. The solids were washed with minimal methanol and dried to afford an additional 16.1 g (20.5%) of the title compound of Preparation B.

Preparation C 2,4-Dichloro-6-methyl-1-oxy-nicotinic acid methyl ester. Urea hydrogen peroxide addition compound (98% pure) (3.860 g, 40.9 mmol) was added to a stirring solution of 2,4-dichloro-6-methyl-nicotinic acid methyl ester (3.000 g, 13.6 mmol) in trifluoroacetic acid (15 ml) under nitrogen. The reaction mixture was stirred at room temperature for 18 hr. Additional urea-hydrogen peroxide addition compound (0.640 g, 6.8 mmol) was added and the reaction stirred for an additional 3 hr. Reaction mixture was poured over ice-water and stirred rapidly. The mixture was treated with sodium thiosulfate, adjusted to pH 11 with 2N aqueous NaOH and extracted 3 times with chloroform. The combined chloroform extracts were washed with water, brine, dried over sodium sulfate and concentrated to give 2.98 g (93%) of the title compound of Preparation C. $^1$H NMR ($CDCl_3$) δ 7.26 (s,1H), 3.98(s,3H), 2.54(s,3H) ppm.

Preparation D

4-Chloro-6-methyl-2-(2,4,6-trimethyl-phenoxy)-1-oxy-nicotinic acid methyl ester. A mixture of 2,4-dichloro-6-methyl-1-oxy-nicotinic acid methyl ester (prepared as described in Preparation C, 2.240 g, 9.49 mmol) and 2,4,6-trimethylphenol (1.290 g, 9.49 mmol) in dry THF was cooled in ice bath and 60% NaH in oil (380 mg, 9.49 mmol) was added in a portionwise during a period of 5 min. The reaction mixture was stirred at room temperature for 6 hr. The mixture was quenched with water, saturated ammonium chloride and extracted twice with chloroform. The organic layer was dried and concentrated to give 3.120 g (97%) of the title compound of Preparation D which was used directly for the next step reaction. $^1$H NMR ($CDCl_3$) δ 7.04(s,1H), 6.78(s,2H), 3.48(s,3H), 2.52(s,3H), 2.22(s,3H), 2.08(s,6H) ppm Preparation E 4-Chloro-6-methyl-2-(2,4,6-trimethyl-phenoxy)-nicotinic acid methyl ester. To a solution of crude 4-chloro-6-methyl-2-(2,4,6-trimethyl-phenoxy)-1-oxy-nicotinic acid methyl ester (prepared as described in Preparation D, 3.100 g) in 30 ml of dry methylene chloride was added 2M $PCl_3$ in methylene chloride (5.3 ml, 10.6 mmol) at room temperature. The resulting mixture was heated under reflux for 1 hr. The mixture was concentrated to dryness and the residue was poured over ice-water and extracted with $CHCl_3$. The organic layer was dried and concentrated to give 2.82 g (93%) of the crude title compound. The crude material was purified through silica gel column chromatography using $CHCl_3$/Hexane (1:1) as eluent to give 1.4521 g of the title compound of Preparation E as yellow crystals, mp 127–128.5° C. Anal. for $C_{17}H_{18}ClNO_3$ (C,H,N); $^1$H NMR ($CDCl_3$) δ 6.84 (s,2H), 6.82(s,1H), 3.94(s,3H), 2.27(s,3H), 2.25(s,3H), 2.04(s,6H) ppm.

Preparation F 4-(1-Ethyl-propylamino)-6-methyl-2-(2,4,6-trimethyl-phenoxy)-nicotinic acid methyl ester. A mixture of 4-chloro-6-methyl-2-(2,4,6-trimethyl-phenoxy)-nicotinic acid methyl ester (prepared as described in Preparation E, 3.4343 g, 10.74 mmol) and 1-ethyl-propyl-amine (10 ml) in 10 ml of DMSO was heated at 120° C. for 15 hr. The mixture was quenched with water and extracted with ethyl acetate. The organic layer was dried and concentrated to give a yellow solid. The yellow solid was recrystallized with hexane to give 2.519 g (63%) of the title compound of Preparation F as white crystals, mp 106–107.5° C. Anal. for $C_{22}H_{30}N_2O_3$ (C,H,N). $^1$H NMR ($CDCl_3$) δ 8.04(d,1H), 6.85(s,2H), 6.06 (s,1H), 3.85(s,3H), 3.32(m,1H), 2.28(s,3H), 2.10(s,3H), 2.07(s,3H), 1.62(m,4H), 0.95(t,6H) ppm.

We claim:

1. A method for treating heart failure in a mammal comprising administering to said mammal a therapeutically effective amount of 4-(1-ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propyl)-amine, a prodrug thereof or a pharmaceutically acceptable salt thereof or of said prodrug.

2. A method of claim 1 wherein 4-(1-ethyl-propoxy)-3,6-dimethyl-2-(2,4,6-trimethyl-phenoxy)-pyridine or a pharmaceutically acceptable salt thereof is administered.

3. A method of claim 2 wherein 4-(1-ethyl-propoxy)-3,6-dimethyl-2-(2,4,6-trimethyl-phenoxy)-pyridine is administered.

4. A method of claim 2 wherein the mammal is a human.

5. A method of claim 2 wherein the mammal is a companion animal.

6. A method of claim 2 wherein the heart failure is congestive heart failure.

7. A method of claim 6 wherein 4-(1-ethyl-propoxy)-3,6-dimethyl-2-(2,4,6-trimethyl-phenoxy)-pyridine is administered.

8. A method of claim 6 wherein the mammal is a human.

9. A method of claim 8 wherein the congestive heart failure does not worsen.

10. A method of claim 6 wherein the mammal is a companion animal.

11. A method of claim 1 wherein (3,6-dimethyl-2-(2,4,6-trimethyl-phenoxy)-pyridin-4-yl)-(1-ethyl-propyl)-amine or a pharmaceutically acceptable salt thereof is administered.

12. A method of claim 11 wherein (3,6-dimethyl-2-(2,4,6-trimethyl-phenoxy)-pyridin-4-yl)-(1-ethyl-propyl)-amine is administered.

13. A method of claim 11 wherein the mammal is a human.

14. A method of claim 11 wherein the mammal is a companion animal.

15. A method of claim 11 wherein the heart failure is congestive heart failure.

16. A method of claim 15 wherein (3,6-dimethyl-2-(2,4,6-trimethyl-phenoxy)-pyridin-4-yl)-(1-ethyl-propyl)-amine is administered.

17. A method of claim 15 wherein the mammal is a human.

18. A method of claim 17 wherein the congestive heart failure does not worsen.

19. A method of claim 15 wherein the mammal is a companion animal.

20. A pharmaceutical composition comprising (a) 4-(1-ethyl-propoxy)-3,6-dimethyl-2-(2,4,6-trimethyl-phenoxy)-pyridine or (3,6-dimethyl-2-(2,4,6-trimethyl-phenoxy)-pyridin-4-yl)-(1-ethyl-propoxy)-amine, a prodrug thereof or a pharmaceutically acceptable salt thereof or of said prodrug, (b) a congestive heart failure treating agent and (c) a pharmaceutically acceptable carrier or diluent.

21. A pharmaceutical composition of claim 20 wherein said congestive heart failure treating agent is a cardiac glycoside, a loop diuretic, a thiazide diuretic, a potassium ion sparing diuretic, an angiotensin converting enzyme inhibitor, an angiotension receptor antagonist, a nitrovasodilator, a phosphodiesterase inhibitor, a direct vasodilator, an $\alpha_1$-adrenergic receptor antagonist, a calcium channel blocker or a sympathomimetic agent.

22. A pharmaceutical composition of claim 21 comprising 4-(1-ethyl-propoxy)-3,6-dimethyl-2-(2,4,6-trimethyl-phenoxy)-pyridine.

23. A pharmaceutical composition of claim 22 comprising 4-(1-ethyl-propoxy)-3,6-dimethyl-2-(2,4,6-trimethyl-phenoxy)-pyridine.

24. A pharmaceutical composition of claim 23 wherein said calcium channel blocker is amlodipine.

25. A pharmaceutical composition of claim 21 comprising (3,6-dimethyl-2-(2,4,6-trimethyl-phenoxy)-pyridin-4-yl)-(1-ethyl-propoxy)-amine or a pharmaceutically acceptable salt thereof.

26. A pharmaceutical composition of claim 25 comprising (3,6-dimethyl-2-(2,4,6-trimethyl-phenoxy)-pyridin-4-yl)-(1-ethyl-propoxy)-amine.

27. A pharmaceutical composition of claim 26 wherein said calcium channel blocker is amlodipine.

28. A method for treating heart failure in a mammal comprising administering to said mammal a pharmaceutical composition of claim 20.

29. A method of claim 28 wherein said congestive heart failure treating agent is a cardiac glycoside, a loop diuretic, a thiazide diuretic, a potassium ion sparing diuretic, an angiotensin converting enzyme inhibitor, an angiotension receptor antagonist, a nitrovasodilator, a phosphodiesterase inhibitor, a direct vasodilator, an $\alpha_1$-adrenergic receptor antagonist, a calcium channel blocker or a sympathomimetic agent.

30. A method of claim 29 comprising 4-(1-ethyl-propoxy)-3,6-dimethyl-2-(2,4,6-trimethyl-phenoxy)-pyridine or a pharmaceutically acceptable salt thereof.

31. A method of claim 30 wherein the mesylate salt of 4-(1-ethyl-propoxy)-3,6-dimethyl-2-(2,4,6-trimethyl-phenoxy)-pyridine is administered.

32. A method of claim 31 wherein said calcium channel blocker is amlodipine.

33. A method of claim 29 comprising (3,6-dimethyl-2-(2,4,6-trimethyl-phenoxy)-pyridin-4-yl)-(1-ethyl-propoxy)-amine or a pharmaceutically acceptable salt thereof.

34. A method of claim 33 wherein (3,6-dimethyl-2-(2,4,6-trimethyl-phenoxy)-pyridin-4-yl)-(1-ethyl-propoxy)-amine is administered.

35. A method of claim 34 wherein said calcium channel blocker is amlodipine.

36. A kit comprising a. an amount of a compound, said compound being selected from 4-(1-ethyl-propoxy)-3,6-dimethyl-2-(2,4,6-trimethyl-phenoxy)-pyridine, (3,6-dimethyl-2-(2,4,6-trimethyl-phenoxy)-pyridin-4-yl)-(1-ethyl-propoxy)-amine, a prodrug thereof, and a pharmaceutically acceptable salt of said compound or said salt in a first unit dosage form;

b. an amount of a congestive heart failure treating agent; and c. a container.

37. A kit of claim 36 wherein said congestive heart failure treating agent is a cardiac glycoside, a loop diuretic, a thiazide diuretic, a potassium ion sparing diuretic, an angiotensin converting enzyme inhibitor, an angiotension receptor antagonist, a nitrovasodilator, a phosphodiesterase inhibitor, a direct vasodilator, an $\alpha_1$-adrenergic receptor antagonist, a calcium channel blocker or a sympathomimetic agent.

38. A kit of claim 37 comprising 4-(1-ethyl-propoxy)-3,6-dimethyl-2-(2,4,6-trimethyl-phenoxy)-pyridine or a pharmaceutically acceptable salt thereof.

39. A kit of claim 38 wherein 4-(1-ethyl-propoxy)-3,6-dimethyl-2-(2,4,6-trimethyl-phenoxy)-pyridine is administered.

40. A kit of claim 39 wherein said calcium channel blocker is amlodipine.

41. A kit of claim 40 comprising (3,6-dimethyl-2-(2,4,6-trimethyl-phenoxy)-pyridin-4-yl)-(1-ethyl-propoxy)-amine.

42. A kit of claim 41 wherein (3,6-dimethyl-2-(2,4,6-trimethyl-phenoxy)-pyridin-4-yl)-(1-ethyl-propoxy)-amine is administered.

43. A kit of claim 42 wherein said calcium channel blocker is amlodipine.

* * * * *

UNITED STATES PATENT AND TRADEMARK OFFICE
CERTIFICATE OF CORRECTION

PATENT NO. : 6,043,260
DATED : February 10, 1999
INVENTOR(S) : Yuhpyng L. Chen

It is certified that error appears in the above-identified patent and that said Letters Patent is hereby corrected as shown below:

Column 13,
Lines 8, 30 and 34, please replace "(1-ethyl-propoxy)-amine" with
-- (1-ethyl-propyl)-amine --.

Column 14,
Lines 7-8, 10-11 and 19-20, please replace "(1-ethyl-propoxy)-amine" with
-- (1-ethyl-propyl)-amine --.

Signed and Sealed this

Thirtieth Day of December, 2003

JAMES E. ROGAN
*Director of the United States Patent and Trademark Office*